United States Patent [19]

Weikel

[11] 4,197,943
[45] Apr. 15, 1980

[54] DENTAL ALLOY CONTAINER

[76] Inventor: Maurice M. Weikel, 1050 Greenfield Dr., El Cajon, Calif. 92021

[21] Appl. No.: 933,499

[22] Filed: Aug. 14, 1978

[51] Int. Cl.² .............................................. B65D 25/08
[52] U.S. Cl. ..................... 206/219; 366/602; 128/272.1
[58] Field of Search ................ 206/219; 215/DIG. 8; 366/602; 128/272.1

[56] References Cited

U.S. PATENT DOCUMENTS

| | | | |
|---|---|---|---|
| 2,487,236 | 11/1949 | Greenberg | 366/602 |
| 3,451,540 | 6/1969 | Kulischenko | 215/DIG. 8 |
| 3,655,035 | 4/1972 | Muhlbauer | 206/219 |
| 3,762,540 | 10/1973 | Baumann | 206/219 |
| 3,917,062 | 11/1975 | Winters | 206/219 |
| 3,924,741 | 12/1975 | Kachur | 128/272.1 |
| 3,963,120 | 6/1976 | Perfect | 206/219 |

Primary Examiner—Herbert F. Ross
Attorney, Agent, or Firm—Fulwider, Patton, Rieber, Lee & Utecht

[57] ABSTRACT

A dental alloy container is provided with an insert which includes a concave surface that is directed against the blind end of a receptacle to define an isolated, enclosed cavity, separate from the larger enclosure of the container. Access between the larger enclosure and the separate cavity normally exists, except when a threaded barrel is used to force the insert against the blind receptacle end to isolate the cavity. A cap on the container seals the larger enclosure. A drop of mercury can thereby be placed in the isolated cavity and maintained separate from a quantity of silver until it is desired to mix the mercury and silver, immediately prior to use, to form a dental alloy.

6 Claims, 8 Drawing Figures

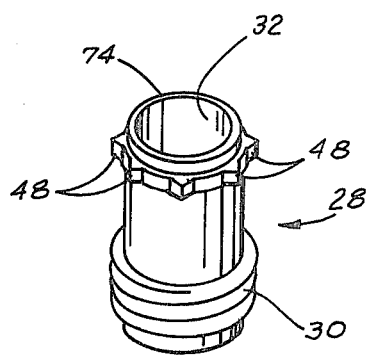
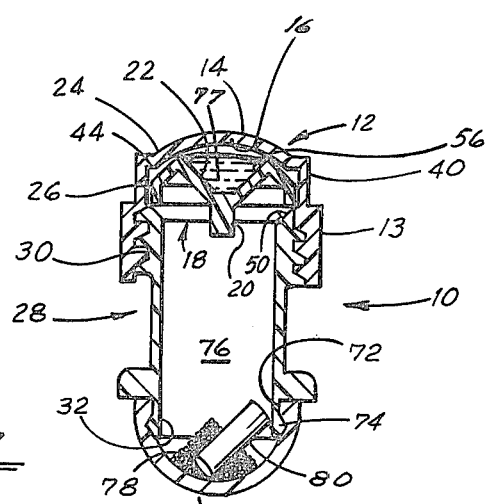
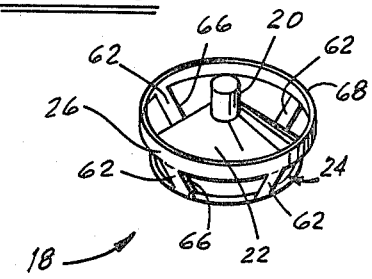
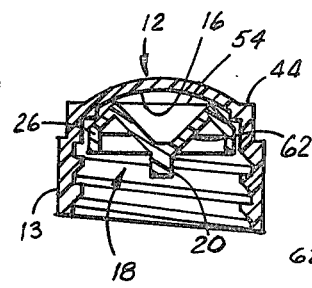
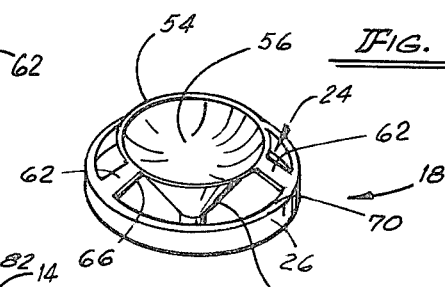
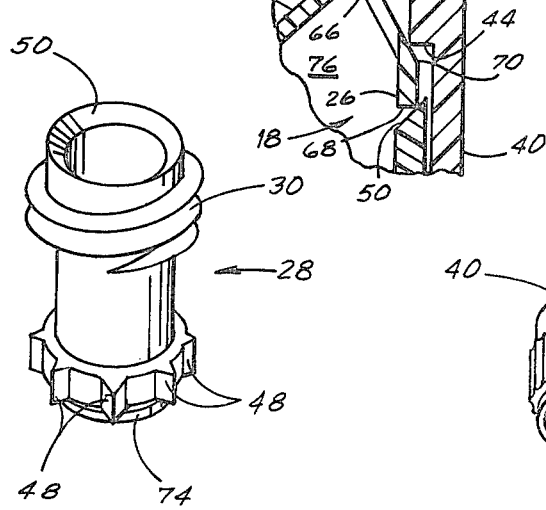
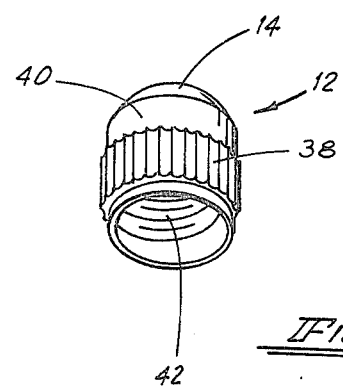

DENTAL ALLOY CONTAINER

BACKGROUND OF THE INVENTION

1. Field of the Invention

The present invention relates to containers for use in packaging, storing and mixing dental amalgams for use by dentists in filling teeth.

2. Description of the Prior Art

Dental alloys are comprised of a mixture of metals which are soft and pliable immediately upon mixing, but which thereafter rapidly harden to form a rigid material for filling cavities drilled in teeth.

In the past, dental alloy capsules have included mercury and silver, which have been stored in a common container until use. However, separation between the alloy metals prior to purposeful mixing has been achieved only with great difficulty. In a conventional dental alloy container, or capsule, the confining structure is typically formed by a receptacle, a separating insert, and an enclosing cover. Typical dental alloys include a small quantity of liquid metallic mercury, and a quantity of a precious metal, such as silver or gold. The precious metal is normally packaged as a quantity of the metal, finely ground to form a powder, and compressed into a pellet. When the mercury and precious metal are mixed together, the mixture forms a dental amalgam or alloy which can be pressed into the vacancy left in a tooth by removal of decayed material. Upon mixing the mercury and precious metal, a dental alloy is formed which is soft and pliable and readily conforms to the configuration of the vacancy, or cavity in a tooth to be filled. Very shortly, however, the alloy permanently hardens, and thereafter forms a hard, durable alloy, highly resistent to chemical reaction or degradation.

Because the amalgam hardens so quickly, it is extremely important for the mercury and precious metal to be maintained in isolation from each other prior to use. With prior dental alloy containers, this has been achieved by first placing a drop of mercury in a concave receptacle, and thereafter placing an insert in the receptacle to define a cavity containing the mercury. The insert is equipped with ports, however, which provide access between the mercury cavity and the overall enclosure within the capsule at the appropriate time. These ports are sealed by the edges of a threaded cover in which the powdered gold or silver pellet and a pestle ultimately used in mixing the amalgam, are first positioned. To effectuate separation of the precious metal from the mercury in packing the container, it is necessary to carefully tilt the receptacle and the cover almost to a horizontal position, and in facing relationship. The two portions are thrust together and rapidly threadably engaged before the mercury is able to leave the cavity defined between the insert and the receptacle and to contact the silver pellet.

To prevent premature contact between the silver and mercury, the silver is compressed into a pellet and a pestle is placed on top of the pellet in the cover. This allows the cover to be tilted farther toward the receptacle without premature mixing. However, it is extremely difficult to obtain a uniform weight from pellet to pellet of the silver. In the manufacture of pellets, a cavity is first filled with powdered silver, the cavity is leveled, and the silver is compressed. The weight between pellets may vary by as much as 15 to 20 miligrams, however. This leads to inconsistencies in the alloy properties after ultimate mixing.

With deft manual dexterity, the task of packaging the mercury and silver pellets separately from each other in conventional containers can be performed. However, any hesitancy in tightening the cover to the receptacle, or tilting of either the cover or receptacle to far toward the horizontal will result in contact between the mercury and the precious metal, so that the quantity of amalgam formed hardens rapidly and becomes useless.

SUMMARY OF THE INVENTION

It is an object of the present invention to provide a dental container which can be used to maintain alloy components separate from each other for prolonged periods, but without the prior requirement for rapid and accurate manual manipulation which have heretofore been necessary, and without the requirement for pelletizing the silver. Rather, according to the present invention, the unitary cover, found in prior art devices, is replaced by a threaded barrel and a separate cap. As a consequence, the component materials of the dental alloy can be easily packed in isolation from each other within the dental container.

As with the prior art device, mercury is first introduced into the receptacle and the separating insert moved into position therein. However, and contrary to prior devices, the silver is not then introduced. Rather, the receptacle is maintained in a position facing concave upward, and the barrel is threadably engaged therewith, whereby interaction between the barrel, receptacle and the insert isolates the cavity containing the mercury from the or sure fingered handling remainder of the container enclosure. No particular haste is required to effectuate this isolation. When the barrel has been firmly engaged with the receptacle, the silver is for the first time introduced into the container on the opposite side of the insert from the mercury. The silver is not in the form of a pellet, but rather is powder, accurately weighed to within one or two miligrams. A stainless steel pestle may also be introduced, as this is useful in mixing the amalgam just prior to use. However, with the high energy amalgamators currently available, a pestle may not be necessary. In any event, a cap is thereafter to the open end of the barrel, and the container serves as a self-contained storage medium until it is desired to mix the amalgam. At that time, the barrel and receptacle are mutually twisted to slightly loosen the threaded engagement therebetween. The container is tipped on its side to allow the mercury to escape its former confinement within the cavity between the insert and the blind end of the receptacle, and to mix with the precious metal in the remainder of the compartment located between the insert and the cap. The threads are retightened and mixing is performed using an oscillating mixer, so that the pestle mixes the powdered silver completely with the mercury.

DESCRIPTION OF THE DRAWINGS

The invention may be explained with greater clarity and facility by reference to the accompanying drawings.

FIG. 1 is a perspective view of the barrel of the container of the invention from above one end.

FIG. 2 is a side elevational sectional view of the container of the invention.

FIG. 3 is an isolated perspective view of the container insert from one side.

FIG. 4 is an isolated perspective view of the container insert from the side opposite the view of FIG. 3.

FIG. 5 is a perspective view of the container barrel from the threaded end, opposite that of FIG. 1.

FIG. 6 is an isolated perspective view of the receptacle of the container.

FIG. 7 is a sectional elevational view of the container receptacle and insert in the absence of engagement with said barrel.

FIG. 8 is a detailed view illustrating interaction of the container receptacle, insert and barrel.

DESCRIPTION OF THE EMBODIMENT

With reference to FIG. 2, a dental alloy container 10 is illustrated having a cup shaped receptacle 12 with a configured annular interiorally threaded skirt 13 and a dome-shaped end enclosure 14 having a shallow concave interior surface 16 at the blind end therein. An insert 18 has a central axial hub 20 which flares to a conical dish-shaped structure 22 with walls that diverge toward the blind end of the receptacle 12 to meet the concave surface 16. The outer periphery of the insert 18 is turned backward in a reverse orientation from the dish 22 to form a webbing 24 which connects the dish 22 to an annular rim 26. A barrel 28 is exteriorly threaded at one end at 30, depicted in FIGS. 1 and 5, and includes an opposing open end 32, depicted in FIG. 1. A hemispherical cap 34 is fixed in position over the open end 32 of the barrel 28, as illustrated in FIG. 2.

The exterior of the receptacle 12 is illustrated in FIG. 6. The outer skirt 38 is knurled, to facilitate grasping for manual threaded engagement and disengagement with the barrel 28. The internal threads 42 are located radially inwardly from the knurled finger grasp 13. Adjacent to the skirt 38, there is a cylindrical, annular wall 40, across which the dome 14 extends. As best illustrated in FIG. 8, at the junction between the annular wall 40 and the dome 14, there is a radially interiorally directed ledge 44 defined in the interior surface of the receptacle 12 at the blind end thereof.

The exterior of the barrel 28 is depicted in detail in FIGS. 1 and 5. The barrel 28 is formed with an annular tubular wall open at one end 32, visible in FIG. 1, and externally threaded, as at 30 at the opposite end as depicted in FIGS. 1 and 5. The barrel 28 at its threaded end terminates in an edge 50, shaped as the surface of a fustrum of a cone and angled radially inward, with convergence directed at the opposite open end 32 of the barrel. The threads 30 on the external surface of the barrel are of the same diameter and pitch as the threads 42 defined in the interior surface of the skirt 38 of the receptacle 12. The barrel 28, and the receptacle 12 can thereby easily be threadably engaged together in the manner depicted in FIG. 2. Spiked protruberances 48 ring the open end 32 of the barrel. Engagement and disengagement of the receptacle 12 and barrel 28 is achieved by grasping the knurled skirt 13 in one hand, by positioning one's fingers among the spiked protruberances 48 with the other hand. Relative twisting thereby produces either engagement or disengagement of the threads 30 and 42.

The container insert 18 as depicted in detail in FIGS. 3 and 4. The insert 18 is formed with the central dish-shaped structure 22 having a central depression delineated by a circular sealing edge 54 and a forming a concave surface 56, as depicted in FIG. 4. Opposite the concave surface 56, and centered relative thereto, the axial hub 20 extends away from the blind end of the receptacle 12 and is useful for centering the insert 18 within the receptacle 12.

The webbing 24, formed with spokes 62 extends outwardly and at an angle from the sealing edge 54. The spokes 62 are connected to the circumferentially positioned rim 26 which is longitudinally displaced from the sealing edge 54. When the rim 26 is in position, as depicted in FIG. 2, it is located away from the blind end formed by the concave surface 16 of the receptacle 12 and near the interior surface of the skirt 13. That is, the rim 26 is displaced from the central structural 22 longitudinally away from the blind end 14 of the receptacle 12. The rim 26 is radially coaxial relative to the disposition of the sealing edge 54 in the barrel 28 and of a larger diameter than the sealing edge 54. Interstitial spaces at 66 are defined between the webbing spokes 62, the rim 26, and the sealing edge 54, as depicted in FIG. 8. The surface 68 of the rim 26 remote from the concave surface 56 is a transverse surface which defines a bearing shoulder. Opposite the bearing shoulder 68, rim 26 includes an edge 70, depicted in FIGS. 4 and 8, which is angled inwardly toward the blind end of the receptacle 12. When the insert 18 is in position in the receptacle 12, the angled edge 70 resides in a circular line of contact against the inwardly directed ledge 44 of the receptacle 12. Similarly, the angled edge 50 of the barrel 28 resides in a circular line of contact with the transverse edge 68 of the insert 18, also as depicted in FIG. 8. Movement of the barrel 28 further into engagement with the receptacle 12 will bring the sealing edge 54 into contact with the concave surface 16, as depicted in FIG. 2. When threaded engagement is loosened, the resiliency of insert 18 draws edge 54 away from concave surface 16, as depicted in FIG. 8.

As illustrated in FIG. 2, the cap 34 is a hemispherical cap which includes a radially inwardly directed circular lip 72. The cap 34 is sufficiently yieldable so that pressure thereon against the open end 32 of the barrel 28 will deflect the lip 72 in the structure of the cap 34 radially outward so that it will pass over a corresponding collar 74 at the open end 32 of the barrel 28. Once past the collar 74, the lip 72 snaps back into place so that the cap 34 remains firmly in position on the barrel 28.

As illustrated in FIG. 2, when completely assembled, the container 10 includes a separate, isolated cavity 64 between the concave surface 56 of the insert 18 and the concave surface 16 of the recess 14. A drop of mercury is normally placed in this cavity prior to before the insert 18 is brought into position in the receptacle 12 and while the receptacle 12 is inverted from the position of FIG. 2. An enclosure 76 of much larger volume is defined between the insert 18 and the barrel 28 and is covered by the cap 34. An accurately weighed quantity 78 of loose, powdered silver and a solid cylindrical stainless steel pestle 80 are confined within the enclosure 76.

In the utilization of the container 10 of the invention, the receptacle 12 is first inverted from the positions of FIG. 2 and 6. A drop of mercury 77 is placed in the inverted receptacle 12. The insert 18 is then moved into the position with the concave surfaces 16 and 56 in face to face relationship to delineate the cavity 64. While in this position the receptacle 12 and the insert 18 are in the relative positions depicted in FIG. 7, and in greater detail in FIG. 8. It should be noted, by observation of FIG. 8, that a path of communication exists between the cavity 64 and the enclosure 76 through a channel at 82 past the sealing edge 54 of insert 18 and through the interstitial spaces 66. Therefore, unless of this passageway is closed, the mercury 77 in the cavity 22 is able to escape therefrom, and prematurely mix with the silver powder 78. To prevent this, the barrel 28 is threadably engaged with the receptacle 12, with the threads 30 and 42 coacting to draw the barrel 28 toward the blind end of the receptacle 12. As noted in FIG. 8, threaded engagement in this fashion causes angled surface 50 to force the rim 26 of the insert 18 both radially inward and toward the blind end of the receptacle 12. Sufficient tightening of the threads will bring the sealing edge 54 into contact with the concave surface 16 where it establishes a liquid tight seal to isolate the cavity 64 from the enclosure 76. When this is accomplished, the mercury 77 is totally entrapped within the cavity 64.

The silver powder 78 and pestle 80 are then inserted through the opening 32 of the barrel 28 and into the enclosure 76. The cap 34 is snapped into place, with the lip 72 of cap 34 locked over the collar 74 of barrel 28. The container 10 can then be shipped, stored, and moved to any orientation, even the inverted orientation of FIG. 2, without any contact between the mercury 77 in the cavity 64 and the silver powder 78 in the enclosure 76. The sealing edge 54 prevents the mercury 77 from reaching the interstitial gaps 66.

To mix the amalgam, the barrel 28 need merely be disengaged approximately ½ turn from full engagement with the receptacle 12 from the fully engaged position of FIG. 2. Upon shaking, the mercury 77 can then escape the cavity 22 through the slot formed at 82, past the sealing edge 54, through the interstital gaps 66, and into the enclosure 76 to mix with the silver 78.

The barrel 28 is then again fully engaged with the receptacle 12 by complete re-engagement of the threads 30 and 42. The container 10 is normally shaken so that the pestle 80 and completely the mercury 77 and the silver 78. This mixing step is normally performed in an oscillating machine designed for this purpose, commonly found in dental offices.

Once mixing is complete, the threads 30 and 42 of the barrel 28 and receptacle 12 respectively are then totally disengaged and the receptacle 12 is removed. The amalgam remaining in the enclosure 76 can then be extracted and used immediately.

Undoubtedly, numerous other variations and modifications of the invention will become apparent to those familiar with dental alloys and their storage preparation. Accordingly, the invention should not be considered as limited to the specific embodiment depicted herein, but rather is defined in the claims appended hereto.

I claim:
1. A dental alloy container comprising:
A receptacle having a blind end with a concave interior surface and internally threaded cylindrical walls extending longitudinally therefrom,
an insert having a central structure with a sealing edge defining the perimeter of a concave surface disposed in face-to-face relationship with said concave interior surface of said receptacle and with a rim displaced from said central structure longitudinally away from said blind end of said receptacle, said rim having a transverse bearing shoulder means, and with a web joining said rim to said central structure,
a tubular barrel open at one end and with external threads and terminating in a bearing edge at the other end, and threadably engageable with said cylindrical walls of said receptacle so that said bearing edge is able to act longitudinally against said shoulder means, and
cap means for sealing said open end of said barrel, whereby fully threaded engagement of said barrel with said receptacle forces said bearing edge against said insert bearing shoulder means toward said blind end of said receptacle, thereby pressing said sealing edge of said central insert structure into sealed contact with said concave interior surface of said receptacle to form an isolated, enclosed cavity between said concave surfaces of said blind end of said receptacle and said insert, and whereby release of said inner engaged threads allows said sealing edge of said central insert structure to draw away from said concave surface of said blind end of said receptacle to open said cavity.

2. The dental alloy container of claim 1 further characterized in that said cap includes a radially inwardly directed lip for snap fitting onto said barrel.

3. The dental alloy container of claim 1 further characterized in that said rim is displaced radially outwardly from the axial alignment of said sealing edge with said barrel.

4. A dental alloy container according to claim 1 further characterized in that said central structure sealing edge is circular and said rim is radially coaxial relative thereto and of a larger diameter, and said interconnecting web is formed with interstitial gaps therein.

5. The dental alloy container of claim 4 further characterized in that said rim includes an edge directed toward said blind end that is angled inwardly toward said blind end of said receptacle, and said receptacle includes an interiorally directed ledge against which said angled edge of said rim resides in a circular line of contact.

6. The dental alloy container of claim 4 further characterized in that said threaded end of said barrel terminates in an edge angled radially outwardly to contact said bearing shoulder of said rim and force said rim inwardly and toward said blind end of said receptacle upon tightening the threaded engagement of said barrel and said receptacle.

* * * * *